United States Patent [19]

Mourant et al.

[11] Patent Number: 5,498,259
[45] Date of Patent: Mar. 12, 1996

[54] METHOD FOR FUSING BONE

[75] Inventors: Judith R. Mourant, Los Alamos; Gerhard D. Anderson, Velarde; Irving J. Bigio; Tamara M. Johnson, both of Los Alamos, all of N.M.

[73] Assignee: The Regents of the University of California, Alameda, Calif.

[21] Appl. No.: 221,422

[22] Filed: Mar. 31, 1994

[51] Int. Cl.$^6$ .............................. A61F 2/28; A61B 17/36
[52] U.S. Cl. .............................. 606/8; 606/214; 607/88; 128/898
[58] Field of Search ................................ 606/213, 214, 606/8, 27, 28, 40; 128/898; 607/88, 89, 100

[56] References Cited

U.S. PATENT DOCUMENTS

| | | | |
|---|---|---|---|
| 4,932,973 | 6/1990 | Gendler | 623/16 |
| 5,011,495 | 4/1991 | Hollinger | 623/16 |
| 5,236,456 | 8/1993 | O'Leary et al. | 623/16 |

OTHER PUBLICATIONS

R. Schober et al., "Laser–Induced Alteration of Collagen Substructure Allows Microsurgical Tissue Welding," Science 232, 1421 (1986).

Roy S. Chuck et al., "Dye–Enhanced Laser Tissue Welding," Lasers in Surgery and Medicine 9, 471 (1989).

Mehmet C. Oz et al., "Indocyanine Green Dye Enhanced Vascular Welding with the Near Infrared Diode Laser," Vascular Surgery 24, 564 (1990).

Lawrence S. Bass et al., "Changes in Type I Collagen Following Laser Welding," Lasers in Surgery and Medicine 12, 500 (1992).

Rodney A. White et al., "Biological Effects of Laser Welding on Vascular Healing," Lasers in Surgery and Medicine 6, 137 (1986).

M. M. Judy et aL., "Heat–Free Photochemical Tissue Welding with 1,8–naphthalimide Dyes Using Visible (420 nm) Light," SPIE 1876, 175 (1993).

Nader Moazsami et al., "Reinforcement of Colonic Anastomoses with a Laser and Dye–Enhanced Fibrinogen," Arch. Surg. 125, 1452 (1990).

*Primary Examiner*—Stephen C. Pellegrino
*Assistant Examiner*—Sonya Harris Ogugua
*Attorney, Agent, or Firm*—Samuel M. Freund

[57] ABSTRACT

Method for fusing bone. The present invention is a method for joining hard tissue which includes chemically removing the mineral matrix from a thin layer of the surfaces to be joined, placing the two bones together, and heating the joint using electromagnetic radiation. The goal of the method is not to produce a full-strength weld of, for example, a cortical bone of the tibia, but rather to produce a weld of sufficient strength to hold the bone halves in registration while either external fixative devices are applied to stabilize the bone segments, or normal healing processes restore full strength to the tibia.

8 Claims, No Drawings

METHOD FOR FUSING BONE

This invention was made with Government support under Contract No. W-7405-ENG-36 awarded by the U.S. Department of Energy to the Regents of the University of Calif. The Government has certain rights in the invention.

FIELD OF THE INVENTION

The present invention relates generally to the joining of bone fragments, and more particularly to the fusion of bone using electromagnetic radiation.

BACKGROUND OF THE INVENTION

Laser techniques for welding soft tissue have been in development for about thirty years. See, for example, "Biological Effects of Laser Welding on Vascular Healing," by Rodney A. White et al., Lasers in Surgery and Medicine 6, 137 (1986). The general procedure is to utilize a laser to locally sufficiently heat the tissue to be welded at the site of a surgical closure, such that the tertiary structure of bonding proteins occurs without significant chemical damage thereto. In "Heat-Free Photochemical Tissue Welding With 1,8-naphthalimide Dyes Using Visible (420 nm) Light," by M. M. Judy et al., SPIE 1876, 175 (1993), the authors synthesized a class of photochemical dyes which function as photoalkylation agents following activation with visible light. The activated species react readily with nucleophilic amino acid residues, and have been used to bond collagenous dura mater sheets to each other with weld shear strengths of up to 425 $g/cm^2$. Moreover, in "Reinforcement Of Cholonic Anastomoses With A Laser And Dye-Enhanced Fibrinogen," by Nader Moazami et al., Arch. Surg. 125, 1452 (1990), the authors applied indocyanine green dye-enhanced fibrinogen to the serosal surface of two-layer inverting anastomoses, and exposed the surfaces so treated to 808-Nm diode laser radiation. The characteristic drying of the glue to a light brown, and the loss of glistening of the fibrin, indicated the end point. Bursting pressures of the sutured anastomoses without the fibrin glue were significantly less than those anastomoses reinforced with the fibrin glue. The laser-fibrinogen-reinforced suture anastomoses do not require such precise apposition as an anastomosis primarily made by laser. The dye-enhanced fibrinogen absorbs most of the laser energy and thus prevents excessive heating of the substrate tissues. The authors conclude that prevention of anastomotic leakage during the critical first week following surgery should significantly reduce complications associated with such procedures. In "Dye-Enhanced Laser Tissue Welding," by Roy S. Chuck et al., Lasers in Surgery and Medicine 9, 471 (1989), the authors describe the use of a saline solution of fluorescein isothiocyanate in order to reduce the cw argon ion laser energy required for welding, thereby minimizing thermal damage to surrounding, healthy tissue. This concept is supported by Mehmet C. Oz et al. in "Indocyanine Green Dye Enhanced Vascular Welding With the Near Infrared Diode Laser," Vascular Surgery 24, 564 (1990), who state that the minimal injury to tissue within and surrounding the weld may allow more rapid proliferation of myofibroblasts and the deposition of extracellular matrix necessary for regeneration of the vascular tissue at the weld site. Moreover, the authors observe that the 808 nm output of the diode laser is very poorly absorbed by soft tissue. However, this frequency matches the absorption of indocyanine green, and the laser/dye combination can cause substantial and rapid tissue effects.

Although the mechanisms involved in tissue welding are poorly understood, in "Changes In Type I Collagen Following Laser Welding," by Lawrence S. Bass et al., Lasers In Surgery and Medicine, 12, 500 (1992), the authors believe that as a result of absorption of laser light, structural changes occur in the extracellular matrix proteins. They conclude that non-covalent interactions between denatured collagen molecules produced thereby may be responsible for the creation of tissue welding. Irradiation was performed without smoking or charring. In "Laser-Induced Alteration of Collagen Substructure Allows Microsurgical Tissue Welding," by R. Schober et al., Science 232, 1421 (1986), the authors report that histological and fine structural analysis revealed a homogeneous change in collagen with interdigitation of altered individual fibrils as the apparent structural basis of the welding effect.

To date, however, there has been no successful laser welding of hard tissues. The mineral component has greatly different thermal properties than Type I collagen, and likely hinders the welding mechanism thought to be caused by collagen.

Accordingly it is an object of the present invention to provide a method for welding bones using electromagnetic radiation.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for joining bones of this invention includes the steps of chemically removing the calcium from a thin layer of each bone to be joined in the vicinity of the joint to be made, thereby exposing the collagen and heating the region of the joint using electromagnetic radiation.

It is preferred that the removal of the mineral matrix is accomplished using hydrochloric acid.

Preferably also, the method further includes the step of applying a paste, which comprises indocyanine green dye, water, and albumen, to each bone to be joined in the vicinity of the joint before heating the region using electromagnetic radiation.

It is also preferred that the electromagnetic irradiation step is performed using a cw Nd:YAG laser or a diode laser.

Preferably, the region of the joint is lightly carbonized after irradiation.

Benefits and advantages of the present invention include accurate fixation of bone fragments, and extension of current orthopedic techniques to very small bones and to the treatment of fractures within joints. It is further expected that hard tissue welding will result in decreased healing times.

DETAILED DESCRIPTION OF THE INVENTION

Briefly, the present invention is a method for joining hard tissue which includes chemically removing the mineral matrix from a thin layer of the surfaces to be joined, placing the two bones together, and heating the joint using electromagnetic radiation. The goal of the method is not to produce a full-strength weld of, for example, a cortical bone of the tibia, but rather to produce a weld of sufficient strength to hold the bone halves in registration while either external fixative devices are applied to stabilize the bone segments, or normal healing processes restore full strength to the bone.

The following is a description of one successful embodiment of the method, which was applied to the problem of fusing two pieces of chicken tibia in vitro. Cortical bone is fairly universal between species, but an extension of the present method to a human tibia in vivo may require an appropriately different set of parameters, including amounts of acid and the wavelength of electromagnetic radiation.

Diaphysial segments of chicken tibia were prepared by the removal of muscle, tendon, epiphysial ends and periosteum. Two segments were cut from the central part of the tibia in a miter box, with the bone held in an external fixative device to ensure that the central cut was precisely vertical. This cut, which is the interface to be welded, was made with an extra fine coping saw in order to create approximately smooth faces. The outside cuts were made with a fine-bladed hacksaw. The purpose of this procedure was to consistently obtain three parallel cuts on two pieces of bone each about 5 mm in length. These two segments were drilled through in a transverse (radial) direction (in the process of fitting the external fixture). The two precision cut bone ends (cut with the coping saw) were then wiped off with an absorbent paper towel. All further reference to "bone ends" refers to these ends.

The surfaces of the bone ends were sanded using wet/dry 600 paper supported on a glass plate. The purpose of this step was to remove burrs or saw marks which might prevent intimate contact of the bone ends. The bone ends to be welded were placed in 1–3 mm deep solution of 25% commercial muriatic acid solution (approx. 5N HCl) for 5 Seconds in order to decalcify these ends and expose collagen. The specimens were then removed, set on the untreated ends for 60 seconds, and then excess acid was blotted off with paper toweling.

The two treated bone ends were aligned in good apposition in a C-clamp holder and a compressive force of 2 inch-pounds was applied with the C-clamp screw. The C-clamp was subsequently used as a holder for the laser welding procedure, with care taken in handling not to disturb the clamping pressure. About 4.0 watts of continuous 1064 Nm radiation from a cw Nd:YAG laser was carried to the sample by a 400micrometer diameter optical fiber. The unfocused output from the fiber was directed onto the bone interface: the laser beam emerging from the flat fiber face was not characterized. The fiber end was held 1–2 mm from the bone surface at the weld site. The fiber was held in position until the bone showed indications of carbonization (about 10 s) at the surface, then moved circumferentially along the junction to a second spot 1–2 mm away. Again, when light carbonization occurred, the fiber was moved to a new site, and the procedure continued until the bone interface was completely circled.

Following the welding procedure, the fused sample was removed from the clamp and placed in a normal saline solution for 16–24 hours, to ensure rehydration before the strength of the weld was tested. Wire loops were inserted through the holes drilled in each half of the fused pair of bone segments. The loops were used to fasten the segments to a fixed support and a weight holder, and weights were added to the holder until the union failed. As the chicken tibias were of fairly uniform diameter and thickness (of the cortical bone), the gross weight was taken to be indicative of the specific failure tension (g/cm$^2$). A successful weld would hold about 1.0 kg before failing, the maximum observed strength being 1600 g. A variety of bone sample control pairs were tested, including with and without acid treatment, with and without lasing, etc. The only significant union strength was generated in pairs that were normally prepared and acid treated, then clamped for the same amount of time (about 5–10 minutes) but not irradiated. After 16–24 hours of immersion in saline solution, however, the union held less than 500 g before failure. While this was a measurable strength, it was a factor of about three less than the strength of a laser weld. On the other end of the scale, the failure strength of an intact tibia was beyond the weight limits of this technique.

Similar experiments were performed using a diode laser operating at 820 nm. However, for those experiments, a "solder" was used to enhance absorption of laser radiation in the region of joint. Indocyanine green has a broad absorption band peaking at about 804 nm. At the wavelength of the diode laser, absorption is approximately one-half of that at the peak. Dye enhancement of solders used in soft tissue welding by others has been found to improve the selectivity of heating, the localization resulting in less damage to surrounding tissue. A solder consisting of water, albumin and indocyanine green having the constancy of paste was applied to the surfaces to be joined after acid treatment. Rather than irradiating the joint directly with the laser, light was applied slightly above or below the junction. In general, it was found that thicker pastes produced stronger welds.

Overall, there does not appear to be a distinct advantage to using the diode laser/paste procedure over the dry/ Nd:YAG method. It was also found that if the irradiation was terminated before carbonization of the joint, the resulting joints were considerably weaker. It may be that simple collagen bonding, which is assumed to be the principal process in soft tissue welding, is not as important for hard tissue welding. In addition, weld strengths according to the method of the present invention are significantly greater than those obtained for soft tissue welding. That is, bone surface areas employed were approximately 0.5 cm, which yields bone strengths of about 1400g/cm$^2$, as compared to 160 g/cm$^2$ strength reported for welding rat tail tendons.

A paste including bone dust and saline solution was observed to give similar results to those obtained using indocyanine green dye.

The foregoing description of the invention has been presented for purposes of illustration and description and is not intended to be exhaustive or to limit the invention to the precise form disclosed, and obviously many modifications and variations are possible in light of the above teaching. Clearly, it would be apparent to one having ordinary skill in the art of laser welding of tissues, after having studied the present disclosure, that the method for fusing bone hereof could be applied to repair of bone fractures.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for joining bones at a chosen location, which comprises the steps of:

a. chemically removing the mineral matrix from a thin layer of each bone to be joined at the chosen location, thereby exposing collagen;

b. placing the bones to be joined in contact at the locations so treated; and c. heating the contact using electromagnetic radiation.

2. The method as described in claim 1, wherein said step of removing the mineral matrix from a thin layer at the chosen location is accomplished using hydrochloric acid.

3. The method as described in claim 1, wherein said step of heating the contact using electromagnetic radiation is performed using a diode laser.

4. The method as described in claim 3, further comprising the step of applying a paste which includes indocyanine green dye, water, and albumen, to each bone to be joined to the contact, before said step of heating the contact using laser radiation.

5. The method as described in claim 1, wherein said step of heating the contact using electromagnetic radiation is performed using a cw Nd:YAG laser.

6. The method as described in claim 1, wherein said step of heating the contact using electromagnetic radiation is continued until the contact is lightly carbonized.

7. The method as described in claim 1, further comprising the step of applying a paste which includes bone dust and saline solution to each bone to be joined at the chosen location, before said step of heating the contact using laser radiation.

8. A method for repairing a region fractured bones having opposing faces which comprises the steps of:

a. chemically removing the mineral matrix from a thin layer of each the opposing faces of the bone at the fracture, thereby exposing collagen; and b. heating the faces of the fracture using electromagnetic radiation.

\* \* \* \* \*